United States Patent [19]

Okada et al.

[11] Patent Number: 4,769,124
[45] Date of Patent: Sep. 6, 1988

[54] OXYGEN CONCENTRATION DETECTION DEVICE HAVING A PAIR OF OXYGEN PUMP UNITS WITH A SIMPLIFIED CONSTRUCTION

[75] Inventors: Yasushi Okada, Fujimi; Toyohei Nakajima, Shiki, both of Japan

[73] Assignee: Honda Giken Kogyo Kabushiki Kaisha, Tokyo, Japan

[21] Appl. No.: 894,232

[22] Filed: Aug. 7, 1986

[30] Foreign Application Priority Data

Aug. 10, 1985 [JP] Japan .................................. 60-176254
Aug. 10, 1985 [JP] Japan .................................. 60-176255
Aug. 10, 1985 [JP] Japan .................................. 60-176256

[51] Int. Cl.$^4$ ............................................. G01N 27/46
[52] U.S. Cl. ................................. 204/425; 204/408; 204/426
[58] Field of Search .................... 204/1 S, 421–429

[56] References Cited

U.S. PATENT DOCUMENTS

| | | | |
|---|---|---|---|
| 4,282,080 | 8/1981 | Muller et al. | 204/428 |
| 4,384,935 | 5/1983 | DeJong | 204/426 |
| 4,496,455 | 1/1985 | Linder et al. | 204/412 |
| 4,505,804 | 3/1985 | Mase et al. | 204/426 |
| 4,574,627 | 3/1986 | Sakurai et al. | 204/426 |
| 4,601,793 | 7/1986 | Asayama et al. | 204/426 |
| 4,601,809 | 7/1986 | Kitahara | 204/425 |

Primary Examiner—T. Tung
Attorney, Agent, or Firm—Pollock, VandeSande & Priddy

[57] ABSTRACT

An oxygen concentration detection device having a pair of oxygen pump units includes an oxygen-ion conductive solid electrolyte member a surface of which faces a gas retaining chamber. A measuring gas is introduced through a gas restricted region into the gas retaining chamber. The solid electrolyte member is provided with two pairs of electrodes respectively supplied with a pair of pump currents generated by a current supply circuit. The magnitude of the pump current flowing between the electrodes of one of two pairs of electrodes is controlled so that the voltage difference across the electrodes of the other one of the two pairs of electrodes is maintained at a level corresponding to a reference level. The oxygen concentration in the gas retaining chamber is detected in terms of a sum value of pump currents flowing through the two pairs of electrodes.

5 Claims, 2 Drawing Sheets

OXYGEN CONCENTRATION DETECTION DEVICE HAVING A PAIR OF OXYGEN PUMP UNITS WITH A SIMPLIFIED CONSTRUCTION

BACKGROUND OF THE INVENTION

1. Field of the Invention

The present invention relates to a device for detecting an oxygen concentration, and more particularly to a device for detecting an oxygen concentration in a gaseous body such as exhaust gas of an internal combustion engine.

2. Description of Background Information

For the air/fuel ratio control of an internal combustion engine, air/fuel ratio feedback control systems are generally utilized to assure the purification of exhaust gas and improvements of the fuel economy. In those systems, oxygen concentration in exhaust gas is detected, and an air/fuel ratio of the mixture to be supplied to the engine is feedback controlled toward a target air/fuel ratio in response to a result of the detection of oxygen concentration.

As an oxygen concentration detection device for use in such an air/fuel ratio control system, there are devices of a type capable of producing an output signal whose level is proportional to the oxygen concentration in the object gas. As an example, Japanese Patent Application Laid Open No. 52-72286 discloses an oxygen concentration detection device which includes oxygen-ion conductive solid electrolyte members each having a pair of electrodes thereon. The surface of one of the electrodes of the solid electrolyte member forms a part of a gas retaining chamber into which a gas to be measured (measuring gas) is introduced through an introduction orifice.

In this type of oxygen concentration detection device, the solid electrolyte member and the pair of electrodes together operate as an oxygen pump unit. When a drive current is supplied between the electrodes so that the electrode located on the gas chamber's side operates as a negative electrode, oxygen in the gas filling in the gas retaining chamber is ionized and migrates toward the surface of the electrode operative as a positive electrode. The oxygen ions are released through the surface of the positive electrode in the form of oxygen gas. The critical value of the current which can flow between the electrodes under this condition becomes substantially constant with regard to the change in the magnitude of supply voltage. On the other hand, it becomes proportional to the oxygen concentration in the measuring gas. Therefore, by detecting the magnitude of the critical current, the oxygen concentration in the measuring gas can be detected.

However, with the thus constructed oxygen concentration detection device, the output signal whose magnitude is proportional to the oxygen concentration is obtained only when the air/fuel ratio of the mixture detected in terms of the oxygen concentration in exhaust gas is on the lean side from the stoichiometric air/fuel ratio. Therefore, it was not possible to set a target air/fuel ratio value for the feedback air/fuel ratio control in a rich range of the air/fuel ratio.

Another example of an oxygen concentration detection device which can produce an output signal whose level is proportional to the oxygen concentration in exhaust gas both in the rich range and a lean range of the air/fuel ratio is described, for example, in Japanese Patent Application laid open No. 59-192955. It and which includes a pair of solid electrolyte members each of which is provided with a pair of electrodes. The surface of one of two electrodes provided on each solid electrolyte member respectively forms a part of the gas retaining chamber which in turn communicates with the measuring gas via an introduction orifice. The surface of the other electrode of one of the solid electrolyte members faces an atmospheric air chamber.

For this oxygen concentration detection device, one of the oxygen-ion conductive solid electrolyte members and two of its electrodes are operative as the sensor cell unit for sensing the oxygen concentration; the other one of the oxygen-ion conductive solid electrolyte members and its two electrodes are operative as an oxygen pump unit. With this construction, a drive current is supplied in such a manner that the oxygen-ions in the oxygen pump unit move toward its electrode located on the gas retaining chamber's side when a voltage generated across the electrodes of the oxygen concentration detecting sensor cell element is higher than a predetermined reference voltage. On the other hand, when the voltage across the electrodes of the sensor cell element is lower than the predetermined reference voltage, the drive current is supplied so that the oxygen-ions move toward the electrode which is located on the opposite side of the gas retaining chamber. In this way, the variation of the current value becomes proportional to the oxygen concentration both in the lean range and the rich range of the air/fuel ratio.

However, in this type of oxygen concentration detection device, it was necessary to form an atmospheric air chamber, Also, the configuration of the device was rather complicated and expensive.

OBJECT AND SUMMARY OF THE INVENTION

An object of the present invention is therefore to provide an oxygen concentration detection device which is very accurate in operation and capable of producing an output signal whose variation is proportional to the oxygen concentration both in the lean range and the rich range of the air/fuel ratio.

According to the present invention, the oxygen concentration detection device includes an oxygen-ion conductive solid electrolyte member and two pairs of electrodes provided on the solid electrolyte member. A portion of the solid electrolyte member in which each one of two pairs of electrodes is located forms a part of a gas retaining chamber connected to a gas restricted region through which a measuring gas whose oxygen concentration is to be measured is introduced. The oxygen-ion conductive solid electrolyte member and the two pairs of electrodes provided thereon operate as two oxygen pump units.

According to another aspect of the present invention, the oxygen concentration detection device includes a pair of oxygen-ion conductive solid electrolyte members. One of the oxygen-ion conductive solid electrolyte members is provided with a heater element for heating the other oxygen-ion conductive solid electrolyte member which together with two pairs of electrodes provided thereon forms two oxygen pump units.

According to a further aspect of the present invention, the oxygen concentration detection device includes an oxygen-ion conductive solid electrolyte member and two pairs of electrodes provided thereon which together form a pair of oxygen pump units, one of which operates as an oxygen detection pump unit and the other one of which operates as a drive oxygen pump unit. The device further includes current supplies means which supply a current between the electrodes of the oxygen detection pump unit and a drive current between the electrodes of the drive oxygen pump unit so that a voltage across the electrodes of the oxygen detection pump unit is maintained to be equal to a reference voltage. An output signal indicative of the oxygen concentration in the measuring gas is derived in the form of a summed value of the currents respectively flowing between the electrodes of the oxygen detection pump unit and the electrodes of the drive oxygen pump unit.

DETAILED DESCRIPTION OF THE PREFERRED EMBODIMENT

Figure 1:
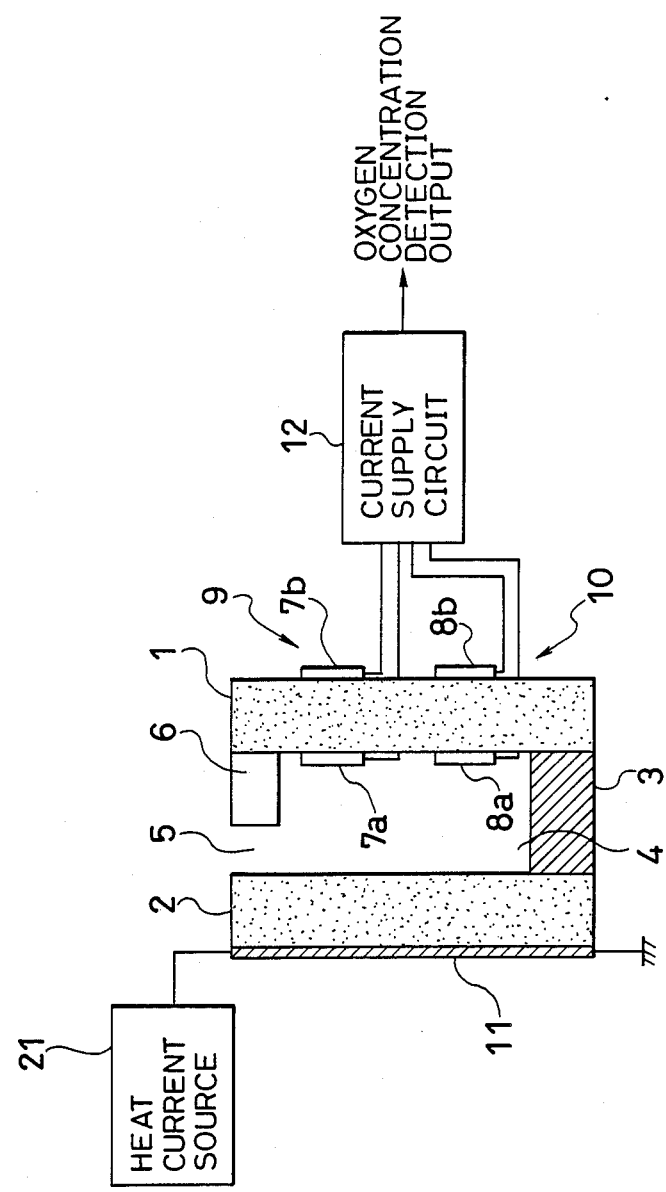
FIG. 1 is a diagram schematically illustrating the construction of the oxygen concentration detection device according to the present invention.

FIG. 1 shows the embodiment of the oxygen concentration detection device according to the present invention. As shown, the device includes a pair of plate-like oxygen-ion conductive solid electrolyte members 1 and 2. Between the electrolyte members 1 and 2, there is provided a spacer 3 which maintains the electrolyte members 1 and 2 apart from each other and in parallel relation with each other. Further, by wall members which are not shown in this figure, a gas chamber 4 is formed so that it operates as the gas retaining chamber. Between ends of the solid electrolyte members 1 and 2, a gas restricted region 5 is formed by means of a stop member 6 so that the measuring gas, i.e. exhaust gas is introduced into the gas chamber 4. The gas restricted region 5 is located in the flow of exhaust gas of the internal combustion engine in a manner that exhaust gas easily flows into the gas chamber 4. Two pairs of electrodes 7a, 7b and 8a, 8b are provided on the oxygen-ion conductive solid electrolyte member 1. The electrodes 7a and 8a are located on a surface of the oxygen-ion conductive solid electrolyte member 1 facing the gas chamber 4. On the other hand, the electrodes 7b and 8b are located on a surface of the oxygen-ion conductive solid electrolyte member 1 on the opposite side of the said surface facing the gas chamber 4. In other words, the oxygen-ion conductive solid electrolyte member 1 is sandwiched between each pair of electrodes 7a and 7b, 8a and 8b.

The oxygen-ion conductive solid electrolyte member 1 and the electrodes 7a and 7b together form a drive oxygen pump unit 9. Similarly, the oxygen-ion conductive solid electrolyte member 1 and the electrodes 8a and 8b together operate as an oxygen detection pump unit 10. On the surface of the oxygen-ion conductive solid electrolyte member 2, which is on the opposite side of the gas chamber 4, there is provided a heater element 11.

Drive currents (or pump currents) from a current supply circuit 12 are supplied to the drive oxygen pump unit 9 and the oxygen detection pump unit 10.

Figure 2:
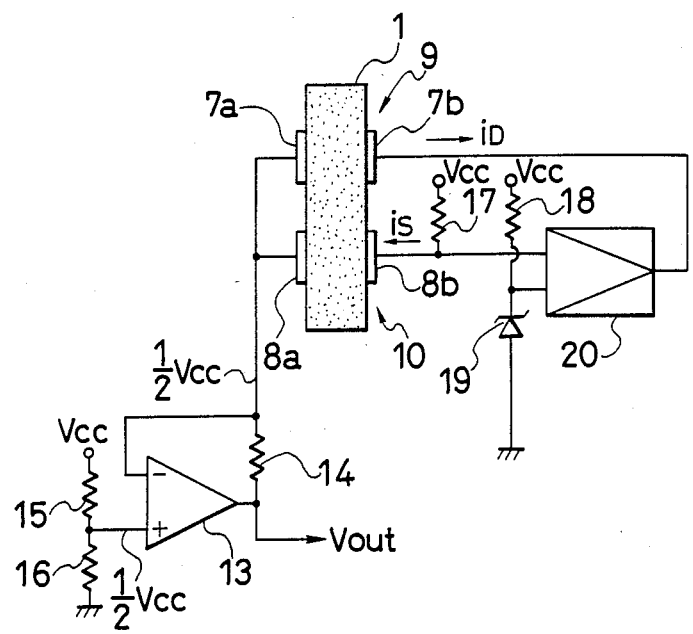
FIG. 2 is a circuit diagram of a current supply circuit of the oxygen concentration detection device shown in FIG. 1.

FIG. 2 illustrates the construction of the current supply circuit 12 for the oxygen concentration detection device of FIG. 1, and in which only the oxygen-ion conductive solid electrolyte member 1 is illustrated for the explanatory purpose.

As shown in FIG. 2, the current supply circuit 12 is made up of an operational amplifier 13, resistors 14 through 18, a zener diode 19, and a difference amplifier 20. An output terminal of the operational amplifier 13 is connected to the electrodes 7a and 8a through the resistor 14, and also connected to an inverting input terminal of the operational amplifier 13. On the other hand, the zener diode 19 is grounded at its cathode. To this zener diode 19, a voltage Vcc is supplied at its anode through the resistor 18 so that a constant reference voltage is produced at its anode. At a non-inverting input terminal of the operational amplifier 13, there is applied a potential Vcc/2 which is produced by dividing the potential Vcc by means of the resistors 15 and 16. To the electrode member 8b, the voltage Vcc is supplied through the resistor 17. One of two input terminals of the difference amplifier 20 is connected to the electrode 8b, and another of its input terminals is connected to the connection line between the resistor 18 and the zener diode 19. An output terminal of the difference amplifier 20 is connected to the electrode 7b.

With the above explained construction, a pump current iD flows through the drive oxygen pump unit 9 and a pump current iS flows through the oxygen detection pump unit 10 in accordance with the oxygen concentration in the gas retaining chamber 4, the potential difference between the electrodes 7a and 7b and the potential difference between the electrodes 8a and 8b. The operation of the current supply circuit 12 will be further explained in detail in the following description.

In the thus constructed oxygen concentration detection device according to the present invention, a heat current is supplied to the heater element 11 from a heat current source 21 which is illustrated in FIG. 1. With this provision, heat is generated by the heater element 11 and utilized to heat the drive oxygen pump unit 9 and the oxygen detection pump unit 10 up to a suitable temperature level which is higher than the temperature of exhaust gas.

Through one of the electrodes (or a first electrode) of the drive oxygen pump unit 9 and one of the electrodes (or a first electrode) of the oxygen detection pump unit 10 (electrodes 7a and 8a), a drive current having a voltage Vcc/2 is supplied by means of the operational amplifier 13. An output voltage Vout of the operational amplifier 13 is a sum between the voltage Vcc/2 and a voltage across the terminals of the resistor 14. Through the resistor 14, there flows a current which is a sum between the pump current iD flowing between the electrodes of the drive oxygen pump unit 9 and the pump current iS flowing between the electrodes of the oxygen detection pump unit 10. Therefore, assuming that the resistance of the resistor 14 is Rs, then the output voltage $V_{out}$ of the operational amplifier 13 will be expressed as Vcc/2+(iD+iS) Rs.

On the other hand, assuming that the voltage across the electrodes of the oxygen detection pump unit 10 is expressed by Vs and the resistance of the resistor 17 is expressed by Rr, then the current flowing through the electrodes of the oxygen detection pump unit 10 is expressed as (Vcc/2−Vs)/Rr. Since the current iS flows from a second electrode (the electrode 8b) to the first electrode (the electrode 8a) of the oxygen detection pump unit 10, oxygen in the gas chamber is ionized and migrates through the oxygen detection pump element.

At the second electrode $8b$ of the oxygen detection pump unit 10, oxygen is released in the form of oxygen gas. The oxygen in the gas chamber 4 is pumped out in this way.

The difference amplifier 20 produces a voltage $V_1$ ($0 < V_1 < Vcc$) which is proportional to the difference between the voltage appearing between the electrodes of the oxygen detection pump unit 10 and the zener voltage $V_z$ of the zener diode 19. Therefore, by the operation of the difference amplifier 20, the voltage of $Vcc/2 - V_1$ is applied between the electrodes of the drive oxygen pump unit 9. In this way, the current iD flows between the electrodes of the drive oxygen pump unit 9.

When the air/fuel ratio of mixture supplied to the engine has approximately reached the stoichiometric value, the drive oxygen pump unit 9 introduces, from outside, oxygen of an amount which is equal to the amount of oxygen which is pumped out by the oxygen detection pump unit 10, into the gas chamber 4. During this operation, the current iD flows from the first electrode (the electrode $7a$) toward the second electrode (the electrode element $7b$) of the drive oxygen pump unit 9. Because the currents iD and iS are set to be equal in magnitude while their directions are opposite, the sum of the currents iD and iS becomes equal to zero (iD+iS=0). Thus, the voltage Vs is controlled to a predetermined reference voltage of, for example, 0.5 V.

The operation of the device under a condition of lean air/fuel ratio mixture will be discussed hereinafter. Since the amount of oxygen flowing into the gas chamber 4 from the introduction orifice of gas restricted region 5 increases when the air/fuel ratio is lean, the oxygen detection pump unit 10 operates so as to increase the amount of oxygen pumped out, i.e., the current iS between the electrodes of the oxygen detection pump unit 10 is increased. By the increase of the current iS, the voltage Vs decreases to raise the level $V_1$ of the output signal of the difference amplifier 20. By the rise of the voltage $V_1$, the voltage $Vcc/2-V_1$ between the electrodes of the drive oxygen pump unit 9 goes down to decrease the magnitude of the current iD. Therefore, the amount of oxygen introduced to the gas chamber 4 by means of the drive oxygen pump unit 9 is decreased. When the air/fuel ratio becomes leaner, the direction of the flow of the current iD is reversed so that the current flows from the second electrode of the drive oxygen pump unit 9 to the first electrode thereof. At the same time, the drive oxygen pump unit 9 pumps out the air in the gas chamber 4. Therefore, the amount of oxygen pumped out by the oxygen detection pump unit 10 will not be increased and maintained at a constant level. Therefore, the internal resistance of the oxygen pump unit 10 becomes constant. In other words, the current iS is maintained at a value which is attained when the air/fuel ratio is equal to the stoichiometric value. Therefore, the summed value of the currents iD and iS becomes greater than zero (iD+iS>0). In this way, the summed value becomes proportional to the oxygen concentration.

The operation of the system when the air/fuel ratio is in the rich range will now be discussed.

Under this condition, the amount of carbon monoxide flowing into the gas chamber 4 from the introduction orifice of gas restricted region 5 increases. The reaction between the carbon monoxide and the oxygen in the gas chamber 4 produces carbon dioxide. The oxygen in the gas chamber is consumed in this way. In response to the amount of consumption of the oxygen, the current iS between the electrodes of the oxygen detection pump unit 10 decreases to raise the voltage Vs. As a result, the output voltage $V_1$ of the differential amplifier 20 decreases. In response to the decrease of the voltage $V_1$, the voltage between the electrodes of the drive oxygen pump unit 9 $Vcc/2-V_1$ increases to increase the current iD. Therefore, the amount of oxygen introduced to the gas chamber 4 becomes greater than the level attained when the air/fuel ratio of the mixture is at a stoichiometric value. In this way, the amount of oxygen in the gas chamber 4 becomes equal to the amount attained under the stoichiometric air/fuel ratio. This means that the amount of oxygen pumped out by means of the oxygen pump unit 10 is maintained at a constant level instead of being decreased, and as a result, the internal resistance of the oxygen pump unit 10 reaches a constant value.

In short, the current iS is maintained at a level attained under the stoichiometric air/fuel ratio, and the value of iD+iS becomes smaller than zero (iD+iS<0) and the value iD+iS varies in proportion to the oxygen concentration.

Figure 3:
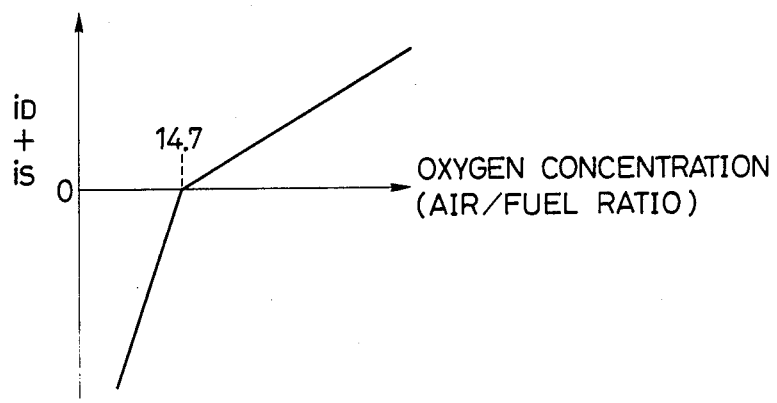
FIG. 3 is a diagram showing an output signal characteristic of the oxygen concentration detection device shown in FIG. 1.

The oxygen concentration detection device according to the present invention is constructed to perform a feedback control for maintaining the oxygen concentration in the gas chamber 4. In such a feedback control, the drive oxygen pump unit 9 operates to pump oxygen out from the gas chamber or pump oxygen into the gas chamber 4 so that the amount of oxygen pumped out by the oxygen detection pump unit 10 is maintained constant. Therefore, the voltage Vs and the current iS across the electrodes of the oxygen detection pump unit 10 are always maintained constant. Thus, the summed value iD+iS varies in proportion to the oxygen concentration both in the lean range and in the rich range as shown in FIG. 3 in which the value 14.7 represents the stoichiometric air/fuel ratio.

The result of detection of the oxygen concentration in this way is obtained in the form of voltage level Vout of the output signal of the operational amplifier 13.

In addition, since the oxygen-ion conductive solid electrolyte member is generally isotropic, a small amount of current may leak between the drive oxygen pump unit 9 and the oxygen detection pump unit 10 in both directions. However, the leak currents are equal in magnitude with each other and the directions are opposite. Therefore, the leak currents are cancelled with each other, and have practically no effect on the oxygen concentration detection current iD+iS.

It will be appreciated from the foregoing, according to the present invention, that an oxygen-ion conductive solid electrolyte member is provided with two pairs of electrodes, and a portion of the oxygen-ion conductive solid electrolyte members in which each one of the two pairs of electrodes is located forms a part of the gas retaining chamber which connects to the measuring gas restricted region. The oxygen-ion conductive solid electrolyte member and two pairs of electrodes together operate as two oxygen pump units. The oxygen pump units are controlled so that one of which is operative to pump oxygen out from the gas retaining chamber or pump oxygen into the gas retaining chamber so that the other oxygen pump unit always pumps a constant amount of oxygen out from the gas retaining chamber. Therefore, a very accurate output signal whose level is proportional to the oxygen concentration in exhaust gas is obtained for air/fuel ratios both in the lean range and the rich range, by detecting the summed value of the currents flowing between the electrodes of each of the oxygen pump units. Further, the oxygen concentration detection device according to the present invention is advantageous in that the construction is relatively simple and the size of the device can be reduced. In addition, the cost of the device is much lower than that of prior art detection devices.

In the case of the preferred embodiment of the present invention which has been described so far, one of two oxygen-ion conductive solid electrolyte members is provided with a heater element. Therefore, very accurate and stable operation of the oxygen concentration detection is enabled by heating the oxygen detection pump element and the drive oxygen pump element to a predetermined suitable temperature level.

Further, in the preferred embodiment of the present invention, the amount of oxygen pumped out by means of the oxygen detection pump unit is maintained constant by an operation of current supplies means which supply currents respectively between electrodes of the oxygen detection pump unit and between the electrodes of the drive oxygen pump element so that the voltage developing across the electrodes of the oxygen detection pump element is made equal to the reference voltage. Thus, an accurate detection of the oxygen concentration is enabled in both the rich range and the lean range of the air/fuel ratio.

What is claimed is:

1. An oxygen concentration detection device comprising:
   an oxygen-ion conductive solid electrolyte member forming a gas restricted region into which a gas whose oxygen concentration is to be measured is introduced;
   first pair of electrodes provided on said oxygen-ion conductive solid electrolyte member, and sandwiching a first part of said oxygen-ion conductive solid electrolyte member;
   second pair of electrodes provided on said oxygen-ion conductive solid electrolyte member, and sandwiching a second part of said oxygen-ion conductive solid electrolyte member adjacent to said first part of said oxygen-ion conductive solid electrolyte member; and
   current supply means for supplying first and second pump currents respectively across said first pair of electrodes and said second pair of electrodes, wherein said current supply means performs a feedback control in which a magnitude of said first pump current is detected and a magnitude of said second pump current is controlled to maintain said magnitude of said first pump current constant.

2. An oxygen concentration detection device as set forth in claim 1, further comprising:
   an additional oxygen-ion conductive solid electrolyte member facing said oxygen-ion conductive solid electrolyte member and defining said gas restricted region together with said oxygen-ion conductive solid electrolyte member; and
   heating means connected to said additional oxygen-ion conductive solid electrolyte member for heating said oxygen-ion conductive solid electrolyte member to a predetermined temperature level.

3. An oxygen concentration detection device as set forth in claim 1, wherein said current supply means includes means for supplying said first pump current across said first pair of electrodes, reference voltage generating means for generating a reference voltage of a predetermined constant level, and voltage generating means for generating an output voltage corresponding to a difference between a voltage generated across said first pair of electrodes and said reference voltage so as to detect said magnitude of said first pump current in terms of said voltage generated across said first pair of electrodes, and means for supplying said second pump current across said second pair of electrodes in accordance with said output signals of said voltage generating means.

4. An oxygen concentration detection device as set forth in claim 3, wherein said means for supplying said first pump current comprises a resistor means inserted between a constant voltage source and one of said first pair of electrodes, and means for maintaining the other one of said first pair of electrodes at a constant voltage level, wherein said voltage generating means comprises a difference amplifier means connected to said reference voltage generating means and said one of said first pair of electrodes, for generating an output signal corresponding to a voltage difference between said reference voltage and a voltage of said one of said first pair of electrodes, and wherein said second pump current supply means comprises means for applying said output signal of said difference amplifier means to one of said second pair of electrodes and means for maintaining a voltage level of the other one of said second pair of electrode constant.

5. An oxygen concentration detection device as set forth in claim 1, wherein said current supply means is adjusted so that said first and second pump currents are equal in magnitude and opposite in polarity when an air/fuel ratio in said gas restricted region is equal to a stoichiometric air/fuel ratio, whereby a sum value of said first and second pump currents represents a detection value of oxygen concentration.

* * * * *